(12) United States Patent
Demmer

(10) Patent No.: US 9,579,512 B2
(45) Date of Patent: Feb. 28, 2017

(54) TECHNIQUES FOR MINIMIZING CURRENT DRAIN IN AN IMPLANTABLE MEDICAL DEVICE

(71) Applicant: Medtronic, Inc., Minneapolis, MN (US)

(72) Inventor: Wade M Demmer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/712,519

(22) Filed: May 14, 2015

(65) Prior Publication Data

US 2016/0279424 A1    Sep. 29, 2016

Related U.S. Application Data

(60) Provisional application No. 62/137,488, filed on Mar. 24, 2015.

(51) Int. Cl.
| | | |
|---|---|---|
| *A61N 1/00* | (2006.01) | |
| *A61N 1/378* | (2006.01) | |
| *A61N 1/365* | (2006.01) | |
| *A61N 1/37* | (2006.01) | |
| *A61N 1/368* | (2006.01) | |

(52) U.S. Cl.
CPC ............. *A61N 1/378* (2013.01); *A61N 1/365* (2013.01); *A61N 1/3708* (2013.01); *A61N 1/3682* (2013.01); *A61N 1/3684* (2013.01); *A61N 1/3688* (2013.01)

(58) Field of Classification Search
CPC ...... A61N 1/378; A61N 1/365; A61N 1/3682; A61N 1/3684; A61N 1/3688; A61N 1/3708
See application file for complete search history.

(56) References Cited

U.S. PATENT DOCUMENTS

| | | | |
|---|---|---|---|
| 4,148,320 A | 4/1979 | Ohara | |
| 4,406,286 A | 9/1983 | Stein | |
| 5,318,593 A | 6/1994 | Duggan | |

(Continued)

OTHER PUBLICATIONS (PCT/US2016/021829) PCT Notification of Transmittal of the International Search Report and the Written Opinion of the International Searching Authority, mailed Jun. 28, 2016, 10 pages.

(Continued)

*Primary Examiner* — George Manuel

(57) ABSTRACT

An implantable medical device includes circuitry for generating and delivering electrical stimulation therapy. A power source is included in the implantable medical device for storage of the energy for the stimulation therapy. Techniques and circuits are provided for minimizing energy losses associated with the storage of the stimulation therapy energy. The implantable medical device circuitry includes charging circuitry that is operated in at least a first mode and a second mode, such that the charging circuit is operable in one of the at least first and second modes based on whether an intrinsic cardiac event is detected. The charging circuit is operable to withhold charging the output capacitor in the first mode until a given cardiac cycle elapses without a sensed intrinsic cardiac event.

20 Claims, 6 Drawing Sheets

(56) References Cited

U.S. PATENT DOCUMENTS

| | | | |
|---|---|---|---|
| 5,447,522 | A | 9/1995 | Chang |
| 6,283,985 | B1 | 9/2001 | Harguth |
| 6,324,425 | B1 | 11/2001 | Blow |
| 6,353,760 | B1 | 3/2002 | Lyden |
| 6,363,283 | B1 | 3/2002 | Lyden |
| 6,411,844 | B1 | 6/2002 | Kroll |
| 6,706,059 | B2 | 3/2004 | Harguth |
| 6,711,437 | B2 | 3/2004 | Thompson |
| 6,892,096 | B2 | 5/2005 | Lyden |
| 7,002,790 | B2 | 2/2006 | Hossick-Schott |
| 7,024,246 | B2 | 4/2006 | Acosta |
| 7,131,988 | B2 | 11/2006 | Harguth |
| 7,212,856 | B2 | 5/2007 | Rossing |
| 7,544,218 | B2 | 6/2009 | Norton |
| 7,570,995 | B1 | 8/2009 | Kroll |
| 7,805,189 | B2 | 9/2010 | Stein |
| 8,352,025 | B2 | 1/2013 | Jacobson |
| 8,755,884 | B2 | 6/2014 | Demmer |
| 8,788,035 | B2 | 7/2014 | Jacobson |
| 2003/0204222 | A1 | 10/2003 | Leinders |
| 2004/0158294 | A1 | 8/2004 | Thompson |
| 2004/0215260 | A1 | 10/2004 | Vonk et al. |
| 2005/0075677 | A1 | 4/2005 | Ganion et al. |
| 2005/0182389 | A1* | 8/2005 | LaPorte .............. A61B 5/0031 604/890.1 |
| 2006/0167503 | A1 | 7/2006 | Warren et al. |
| 2007/0156189 | A1 | 7/2007 | DeGroot et al. |
| 2012/0283795 | A1 | 11/2012 | Stancer et al. |

OTHER PUBLICATIONS (PCT/US2016/021821) PCT Notification of Transmittal of the International Search Report and the Written Opinion of the International Searching Authority, mailed Jul. 1, 2016, 10 pages.

* cited by examiner

US 9,579,512 B2

TECHNIQUES FOR MINIMIZING CURRENT DRAIN IN AN IMPLANTABLE MEDICAL DEVICE

CROSS-REFERENCE TO RELATED APPLICATION

This application claims the benefit of U.S. Provisional Application No. 62/137,488, filed on Mar. 24, 2015. The disclosure of the above application is incorporated herein by reference in its entirety.

Cross-reference is hereby made to the commonly-assigned related U.S. application Ser. No. 14/712,556, entitled "Techniques for Minimizing Current Drain in an Implantable Medical Device," to Demmer, which is filed concurrently herewith and incorporated herein by reference in its entirety.

FIELD OF THE INVENTION

The present invention pertains to implantable medical devices and more particularly to techniques and circuitry for minimizing current drain associated with therapy delivery.

BACKGROUND

The technology explosion in the implantable medical device (IMD) industry has resulted in many new and innovative devices and methods for analyzing the health of a patient and/or providing therapies to improve quality of life. IMDs include pacemakers, implantable cardioverter-defibrillators (ICDs), neural stimulators, drug administering devices, monitors, etc. State-of-the-art IMDs are capable of performing significantly more complex tasks and are vastly more sophisticated and complex than earlier IMDs and their therapeutic benefits have been well established.

Cardiac IPGs and monitors as well as other IMDs are powered by an internal power source, typically one or more batteries, to serve a variety of functions, including, but not limited to, supplying power to electronic components and circuitry and charging high voltage capacitors that are discharged through medical electrical leads into the heart to regulate heart rhythms. The functional sophistication and complexity of the IMD operating systems powered by the power source have increased over the years.

IMDs that are powered by a non-rechargeable power source such as a standalone battery must be replaced when the battery becomes depleted, and therefore conserving the energy in the power source is important to maintain or prolong the life of the IMD. Yet, current drain in a medical device comes from several sources. The "static current" is the current required to run the IMD circuitry (including micro-processor). The "stimulation therapy current" (such as pacing pulse current) is the energy required to deliver therapy. In an IMD, capacitors are charged up in anticipation of delivering a stimulation therapy and the energy in the capacitor is delivered if the stimulation therapy is warranted. However, an intervening sensed event will preclude delivery of the stimulation therapy. Depending on the duration over which the stimulation therapy energy is stored in a capacitor, some of the stored energy will bleed-off from the capacitor. As a result, a significant amount of the power source may be lost from the charged capacitor even without delivery of a stimulation pulse. Therefore, conservation techniques and circuitry are needed to reduce the energy losses associated with storage of stimulation therapy energy in an implantable medical device.

SUMMARY

Techniques and circuits are provided for minimizing energy losses associated with storage of energy for delivery of stimulation therapy. The implantable medical device circuitry includes charging circuitry that is operated in at least a first mode and a second mode, such that the charging circuit is operable in one of the at least first and second modes based on whether an intrinsic cardiac event is detected.

In accordance with an embodiment, an implantable medical device includes a sense amplifier configured to sense intrinsic cardiac events, an output capacitor for storage of stimulation therapy energy, a charging circuit coupled to the output capacitor, and a processor.

In one embodiment, the charging circuit may be operable in a first and a second mode. In the first mode, the charging circuit is controlled to withhold charging of the output capacitor until a given cardiac cycle elapses without a sensed intrinsic cardiac event during operation. In the second mode, the charging circuit is controlled to initiate charging of the output capacitor within the given cardiac cycle prior to elapsing of the given cardiac cycle during operation.

DETAILED DESCRIPTION

As will be outlined in the present disclosure, techniques are employed to minimize the capacitor energy losses that are associated with storage of energy within the capacitor for durations that are longer than necessary. In this disclosure, a cardiac cycle is defined between two successive events from the same chamber. For example, the cardiac cycle may be the interval between two successive atrial events or between two successive ventricular events.

Figure 1:
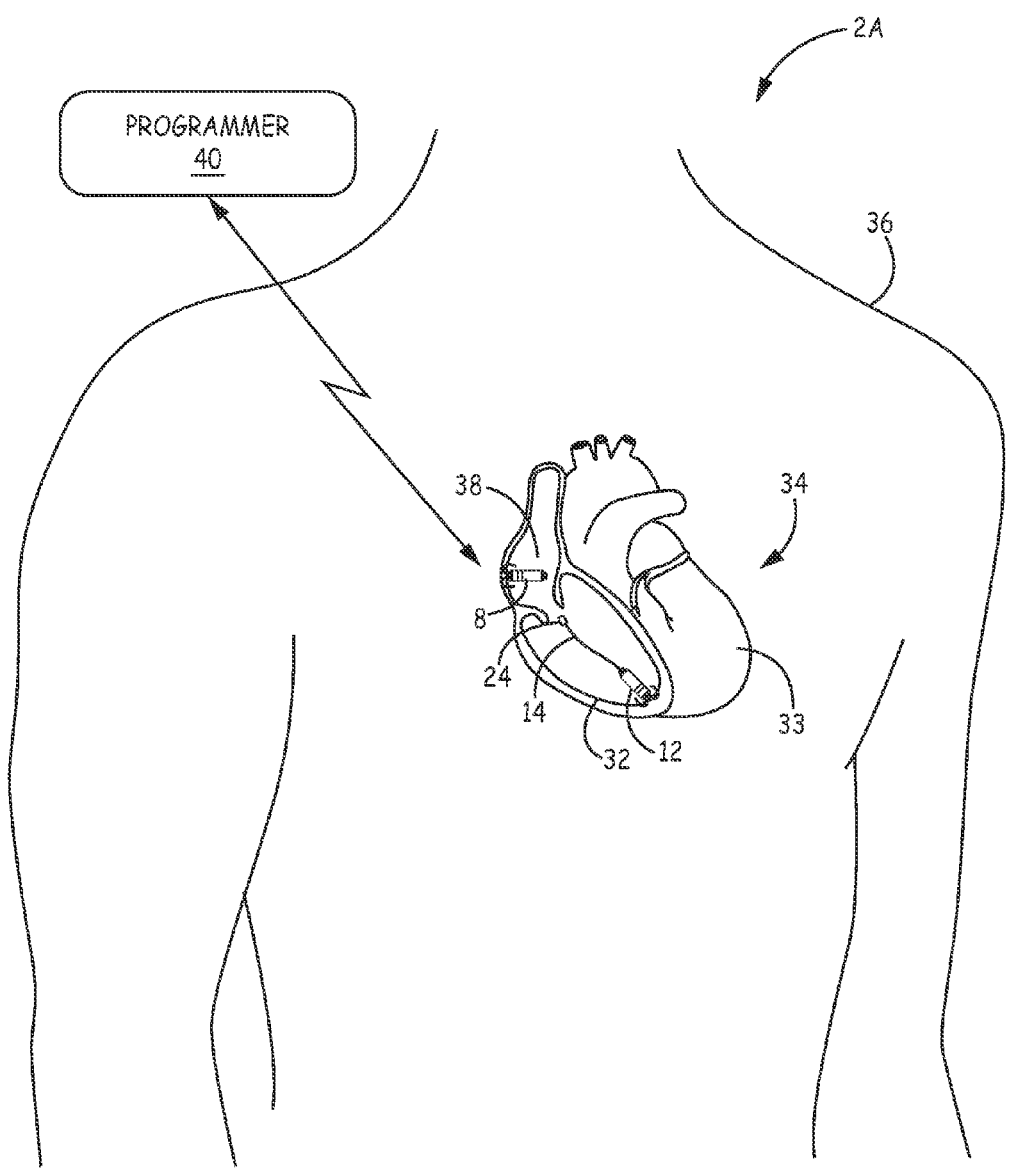
FIG. 1 is a conceptual illustration of an embodiment of an implantable medical system.

FIG. 1 is a conceptual illustration of an example implantable medical system 2A that includes a leadless pacing device (LPD) 8, and optionally an LPD 12 having a sensing extension 14. In the illustrated example, the LPD 8 is implanted in the right atrium 38 of heart 34. In an example, LPD 12 is implanted in right ventricle 32 of heart 34 of patient 36.

Implantable medical system 2 is an example of an implantable medical system configured to coordinate the delivery of ventricular pacing with intrinsic depolarizations of another chamber of the heart. Because LPD 8 is configured to sense intrinsic depolarizations of an atrium, e.g., right atrium 38, implantable medical system 2 is an example of an implantable medical system configured to provide atrio-synchronous ventricular pacing. LPD 8 detects intrinsic depolarizations of atrium 38 and, in response to detecting the intrinsic depolarization of the atrium, delivers an electrical pulse, which may be a pacing pulse delivered during a refractory period of atrium 38 following the intrinsic depolarization of the atrium. LPD 12 is configured to detect, e.g., via electrode 24 on sensing extension 14, the pacing pulse delivered by LPD 8. In response to detecting the electrical pulse from the LPD 8, LPD 12 delivers a pacing pulse to right ventricle 32 in coordination with the intrinsic depolarization of right atrium 38. In some examples, LPD 12 delivers the pacing pulse an AV delay interval after detected the electrical pulse from LPD 8, and thereby provides atrio-synchronous ventricular pacing.

In the example shown in FIG. 1, sensing extension 14 is configured to extend away from LPD 12 and towards right atrium 38 when LPD 12 is implanted in an apex of right ventricle 32. In some examples, sensing extension 14 may have a length that permits sensing extension 14 to remain in right ventricle 32 with LPD 12, as shown in FIG. 1. For example, sensing extension 14 may have a length of about 60 millimeters (as measured from the proximal end connected to LPD 12 and a distal end of electrode 24).

Also shown in FIG. 1 is medical device programmer 40, which is configured to program, and retrieve data from, LPD 8 and LPD 12. Programmer 40 may be a handheld computing device, desktop computing device, a networked computing device, etc. Programmer 40 may include a computer-readable storage medium having instructions that cause a processor of programmer 40 to provide the functions attributed to programmer 40 in the present disclosure. LPD 8 and LPD 12 may wirelessly communicate with programmer 40. For example, LPD 8 and LPD 12 may transfer data to programmer 40 and may receive data from programmer 40. Programmer 40 may also wirelessly program and/or wirelessly charge LPD 8 and LPD 12.

Data retrieved from LPD 8 and LPD 12 using programmer 40 may include cardiac EGMs stored by the LPDs that indicate electrical activity of heart 34 and marker channel data that indicates the occurrence and timing of sensing, diagnosis, and therapy events associated with LPD 8 and LPD 12. Data transferred to LPD 8 and LPD 12 using programmer 40 may include, for example, operational programs for the LPDs that cause the LPDs to operate as described herein. Data transferred to the LPDs may include any programmable parameters of the LPDs or other IMDs described herein, such as the lengths of any intervals or delays described herein, the width and/or amplitude of the electrical pulses delivered by the other IMD, such as LPD 8, and the electrode vectors used by the IMDs to deliver and sense electrical pulses indicative of intrinsic depolarization of another chamber.

Although described herein primarily with respect to the example implantable medical system 2 of FIG. 1, which includes an LPD 8 implanted in right atrium 38, and optionally an LPD 12 implanted within right ventricle 32, the techniques for coordinating delivery of ventricular pacing with intrinsic depolarizations of another chamber of the heart described herein may be implemented in any of a variety of implantable medical systems including any of a variety of IMDs. In some implantable medical device systems, LPD 8 may be replaced by any IMD capable of sensing intrinsic atrial depolarizations and delivering electrical pulses. An example of such an IMD may include a lead-based system such as that shown in FIG. 2.

Figure 2:
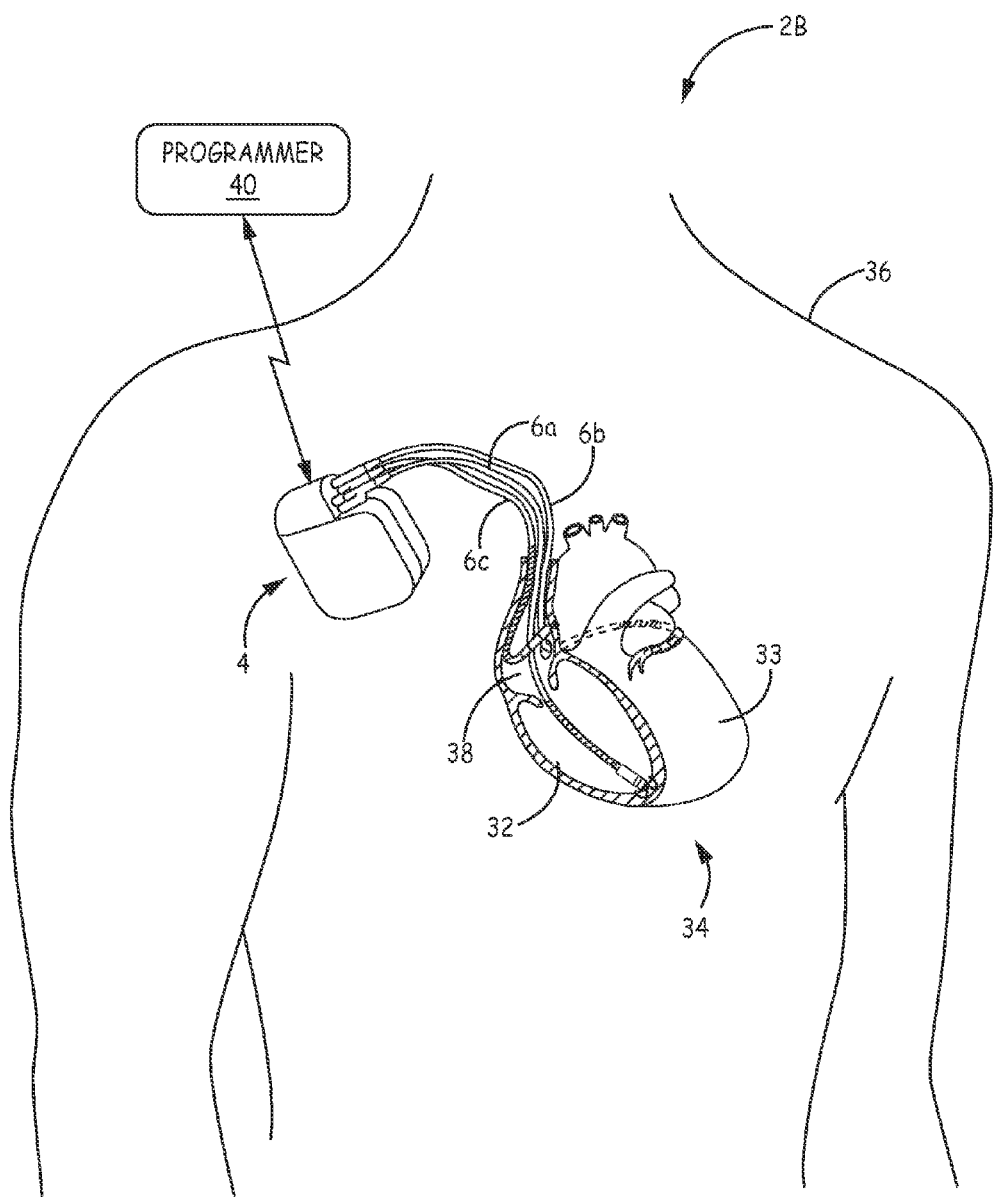
FIG. 2 is a conceptual illustration of an alternative embodiment of an implantable medical system.

FIG. 2 is a conceptual diagram illustrating another example therapy system 2B that may be used to monitor one or more physiological parameters of patient 36 and/or to provide therapy to heart 34 of patient 36. Therapy system 2B includes IMD 4, which is coupled to medical leads 6a, 6b, and 6c, and programmer 40. As referred to herein, each of IMD 4 and medical leads 6a, 6b and 6c may be referred to generally as an IMD. In one example, IMD 4 may be an implantable pacemaker that provides electrical signals to heart 34 via electrodes coupled to one or more of leads 6a, 6b, and 6c. IMD 4 is one example of an electrical stimulation generator, and is configured attached to the proximal end of medical leads 6a, 6b, and 6c. In other examples, in addition to or alternatively to pacing therapy, IMD 4 may deliver neurostimulation signals. In some examples, IMD 4 may also include cardioversion and/or defibrillation functionalities. In other examples, IMD 4 may not provide any stimulation functionalities and, instead, may be a dedicated monitoring device. Patient 36 is ordinarily, but not necessarily, a human patient.

Medical leads 6a, 6b, 6c extend into the heart 34 of patient 36 to sense electrical activity of heart 34 and/or deliver electrical stimulation to heart 34. In the example shown in FIG. 2, right ventricular (RV) lead 6a extends through one or more veins (not shown), the superior vena cava (not shown), right atrium 38, and into right ventricle 32. RV lead 6a may be used to deliver RV pacing to heart 34. Left ventricle (LV) lead 6b may be used to deliver LV pacing to heart 34. Right atrial (RA) lead 6c may be used to deliver RA pacing to heart 34.

In some examples, system 2B may additionally or alternatively include one or more leads or lead segments (not shown in FIG. 2) that deploy one or more electrodes within the vena cava or other vein, or within or near the aorta. Furthermore, in another example, system 2B may additionally or alternatively include one or more additional intravenous or extravascular leads or lead segments that deploy one or more electrodes epicardially, e.g., near an epicardial fat pad, or proximate to the vagus nerve. In other examples, system 2B need not include one of ventricular leads 6a and 6b.

One or more of medical leads 6a, 6b, 6c may include a set of active fixation tines to secure a distal end of the medical lead to a patient tissue. The inclusion of active fixation tines for each medical leads 6a, 6b, 6c is merely exemplary. One or more of medical leads 6a, 6b, 6c could be secured by alternative techniques.

IMD 4 may sense electrical signals attendant to the depolarization and repolarization of heart 34 via electrodes coupled to at least one of the leads 6a, 6b, 6c. In some examples, IMD 4 provides pacing pulses to heart 34 based on the electrical signals sensed within heart 34. The configurations of electrodes used by IMD 4 for sensing and pacing may be unipolar or bipolar.

IMD 4 may also provide neurostimulation therapy, defibrillation therapy and/or cardioversion therapy via electrodes located on at least one of the leads 6a, 6b, 6c. For example, IMD 4 may deliver defibrillation therapy to heart 34 in the form of electrical pulses upon detecting ventricular fibrillation of ventricles 28 and 32. In some examples, IMD 4 may be programmed to deliver a progression of therapies, e.g., pulses with increasing energy levels, until a fibrillation of heart 34 is stopped. As another example, IMD 4 may deliver cardioversion or anti-tachycardia pacing (ATP) in response to detecting ventricular tachycardia, such as tachycardia of ventricles 28 and 32.

As described above with respect to FIG. 1, programmer 40 may also be used to communicate with IMD 4. In addition to the functions described in FIG. 1, a user may use programmer 40 to retrieve information from IMD 4 regarding the performance or integrity of leads 6a, 6b and 6c and may interact with programmer 40 to program, e.g., select parameters for, any additional therapies provided by IMD 4, such as cardioversion and/or defibrillation.

Leads 6a, 6b, 6c may be electrically coupled to a signal generator and a sensing module of IMD 4 via connector block 7. In some examples, proximal ends of leads 6a, 6b, 6c may include electrical contacts that electrically couple to respective electrical contacts within connector block 7 of IMD 4. In some examples, a single connector, e.g., an IS-4 or a DF-4 connector, may connect multiple electrical contacts to connector block 7. In addition, in some examples, leads 6a, 6b, 6c may be mechanically coupled to connector block 7 with the aid of set screws, connection pins, snap connectors, or another suitable mechanical coupling mechanism.

The configuration of system 2B illustrated in FIG. 2 is merely one example. In other examples, a system may include epicardial leads and/or patch electrodes instead of or in addition to the transvenous leads 6a, 6b, 6c illustrated in FIG. 2. Further, IMD 4 need not be implanted within patient 36. In examples in which IMD 4 is not implanted in patient 36, IMD 4 may deliver defibrillation pulses and other therapies to heart 34 via percutaneous leads that extend through the skin of patient 36 to a variety of positions within or outside of heart 34. For each of these examples, any number of the medical leads may include a set of active fixation tines on a distal end of the medical lead in accordance with the techniques described herein.

In addition, in other examples, a system may include any suitable number of leads coupled to IMD 4, and each of the leads may extend to any location within or proximate to heart 34. For example, other examples of systems may include three transvenous leads located as illustrated in FIG. 2, and an additional lead located within or proximate to the left atrium. Other examples of systems may include a single lead that extends from IMD 4 into right atrium 38 or right ventricle 32, or two leads that extend into a respective one of the right ventricle 32 and right atrium 38. Any electrodes located on these additional leads may be used in sensing and/or stimulation configurations. In each of these examples, any number of the medical leads may include a set of active fixation tines on a distal end of the medical lead in accordance with the techniques described herein.

Figure 3:
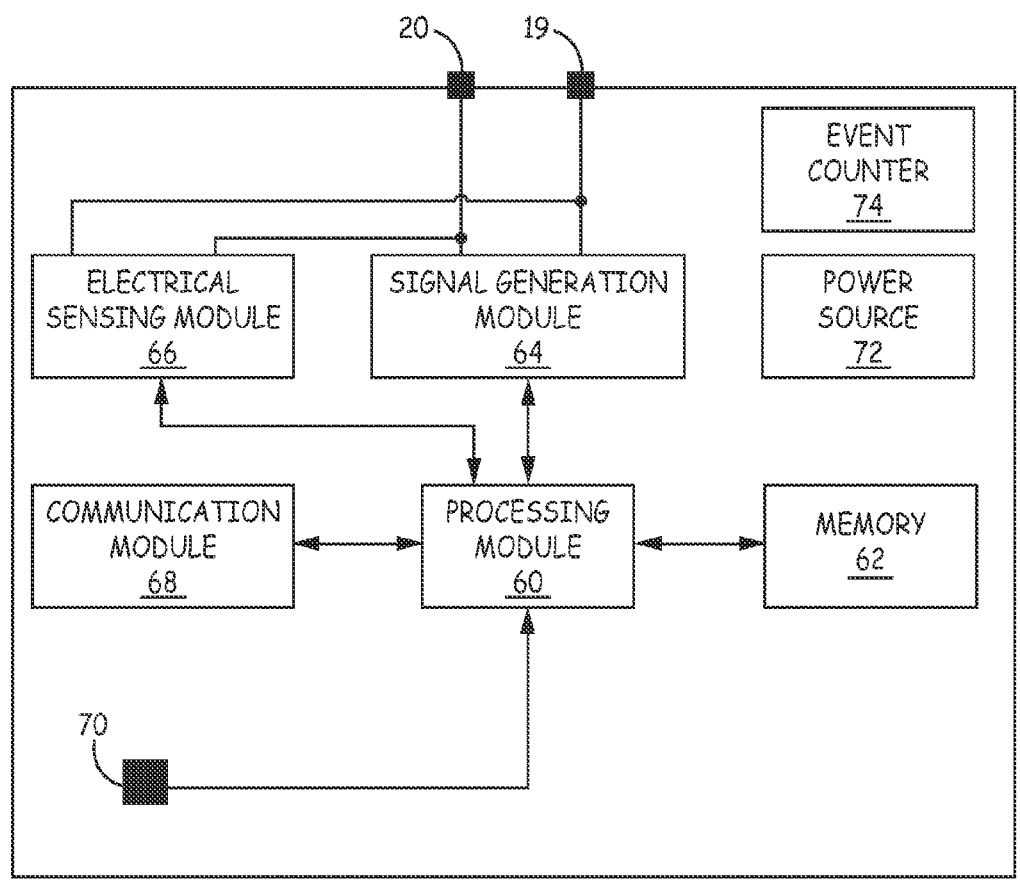
FIG. 3 is a functional block diagram illustrating an exemplary configuration of circuitry of an implantable medical device, such as that illustrated in FIGS. 1 and 2.

FIG. 3 is a functional block diagram illustrating an example configuration of circuitry of any of the aforementioned IMD 4, IMD 8, or IMD 12. The circuitry 16 includes processing module 60, memory 62, signal generation module 64, electrical sensing module 66, communication module 68, sensor 70, and power source 72. Power source 72 may include a battery, e.g., a rechargeable battery or a non-rechargeable standalone battery. In alternative embodiments, power source 72 may additionally include an energy harvester such as the motion-powered energy sources disclosed in commonly assigned U.S. patent application Ser. No. 10/365,893 to Thompson (US Publication Number US2004/0158294), which is incorporated herein by reference.

The modules included in the IMD circuitry represent functionality that may be included in the IMDs of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, and the like. The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

Processing module 60 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry.

Processing module 60 may communicate with memory 62. Memory 62 may include computer-readable instructions that, when executed by processing module 60, cause processing module 60 to perform the various functions attributed to processing module 60 herein. Memory 62 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Furthermore, memory 62 may include instructions that, when executed by one or more processors, cause the modules to perform various functions attributed to the modules herein. For example, memory 62 may include pacing instructions and values for any intervals, delays pulse amplitudes, pulse widths, or the like described herein. The pacing instructions and values may be updated by programmer 40 (FIG. 1).

Signal generation module 64 and electrical sensing module 66 are electrically coupled to electrode contacts 19, 20 for electrodes (not shown) of the IMDs 4, 8, or 12. Processing module 60 is configured to control signal generation module 64 to generate and deliver electrical pulses, or other signals, via electrode contacts 19, 20. The electrical pulses may include electrical pulses to signal intrinsic depolarizations of a chamber of heart 34, e.g., right atrium 38, and pacing pulses to stimulate the chamber, e.g., the right atrium.

In addition, processing module 60 is configured to control electrical sensing module 66 monitor signals from electrode contacts 19, 20 in order to monitor electrical activity of heart 34, e.g., right atrium 38. Electrical sensing module 66 may include circuits that acquire electrical signals. Electrical signals acquired by electrical sensing module 66 may include intrinsic cardiac electrical activity, such as intrinsic atrial depolarizations and/or intrinsic ventricular depolarizations. Electrical sensing module 66 may filter, amplify, and digitize the acquired electrical signals to generate raw digital data. Processing module 60 may receive the digitized data generated by electrical sensing module 66. In some examples, processing module 60 may perform various digital signal processing operations on the raw data, such as digital filtering. Processing module 60 may sense cardiac events based on data or signals received from electrical sensing module 66. For example, in examples in which LPD 8 is implanted in right atrium 8, processing module 60 may sense intrinsic atrial depolarizations, e.g., P-waves, based on data or signals received from electrical sensing module 66.

In some examples, in addition to electrical sensing module 66, the IMD circuitry includes sensor 70, which may comprise at least one of a variety of different sensors. For example, sensor 70 may comprise at least one of a pressure sensor and an accelerometer. Sensor 70 may generate signals that indicate at least one of parameter of patient 12, such as, but not limited to, at least one of: an activity level of patient 36, a hemodynamic pressure, and heart sounds.

Communication module 68 may include any suitable hardware (e.g., an antenna), firmware, software, or any combination thereof for communicating with another device, such as programmer 40 (FIG. 3) or a patient monitor. Under the control of processing module 60, communication module 68 may receive downlink telemetry from and send uplink telemetry to other devices, such as programmer 40 or a patient monitor, with the aid of an antenna included in communication module 68.

Figure 4:
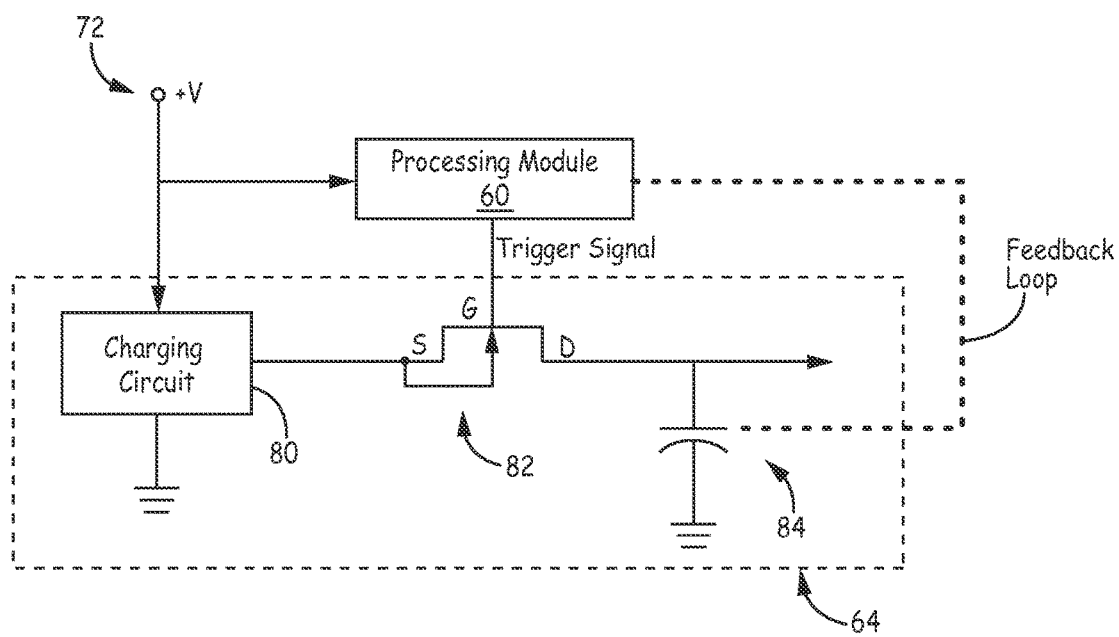
FIG. 4 depicts a portion of the circuitry of FIG. 3 in accordance with an embodiment.

FIG. 4 depicts a portion of the circuitry 16 of FIG. 3 in accordance with an embodiment. In particular, the details of an exemplary signal generation module 64 are illustrated being coupled to the power source 72 and the processing module 60. The signal generation module includes a charging circuit 80 that receives energy from an energy source, such as power source 72. The charging circuit 80 is coupled to an energy storage device 84, such as output capacitor, via a switch 82. The energy storage device 84 is configured to store a voltage that is sufficient to generate electrical energy that is capable of inducing an evoked response (atrial or ventricular) when delivered to tissue of a patient's heart. Nevertheless, it is contemplated that the energy storage device may have a maximum capacity that exceeds the pacing capacity, i.e., energy required for a stimulation pulse voltage that induces an evoked response. In such an implementation, the charging circuit 80 may simply charge up the energy storage device to the pacing capacity rather than the maximum capacity.

In the illustration, the signal generation module 64 is shown being coupled to processing module 60 that issues instructions to control the timing of the charging of the output capacitor 82. The output capacitor 82 is charged by the charging circuit 80 while the conduction path of FET 82 is conductive or closed, which occurs as will be described in detail below.

The processing module 60 will issue a trigger signal of fixed amplitude to the gate of FET 82 to close the gate and initiate the charging of the capacitor 82. The trigger pulse is of a predetermined pulse width defining the pacing pulse width or interval and the FET 82 responds by switching to the closed state from an open state thereby closing the source-drain discharge conduction path. The trigger pulse is of a magnitude that immediately drives the FET into saturation, and the gate remains closed until the capacitor 82 has been charged to the desired capacity.

Accordingly, the processing module 60 receives a feedback signal that indicates the level to which the capacitor 74 has been charged, and this in turn causes the processing module 60 to terminate the charging. The charging is terminated by the return of the FET 82 source-drain conduction path to the open or non-conducting state.

In alternative embodiments, the first energy storage device 82 may be coupled to a second energy storage device (not shown) such that the stimulation pulse voltage is first stored on the first energy storage device 82 prior to being transferred to the second energy storage device. The same principles for controlling the timing of the charging up of the first energy storage capacitor may be employed in such an implementation.

Although capacitor 84 is illustrated as a single discrete component, it should be understood that multiple storage devices may be utilized to store the stimulation pulse voltage. Switch 82 is illustrated as a field effect transistor (FET), but any known switching mechanism may be employed in alternative embodiments.

Figure 5:
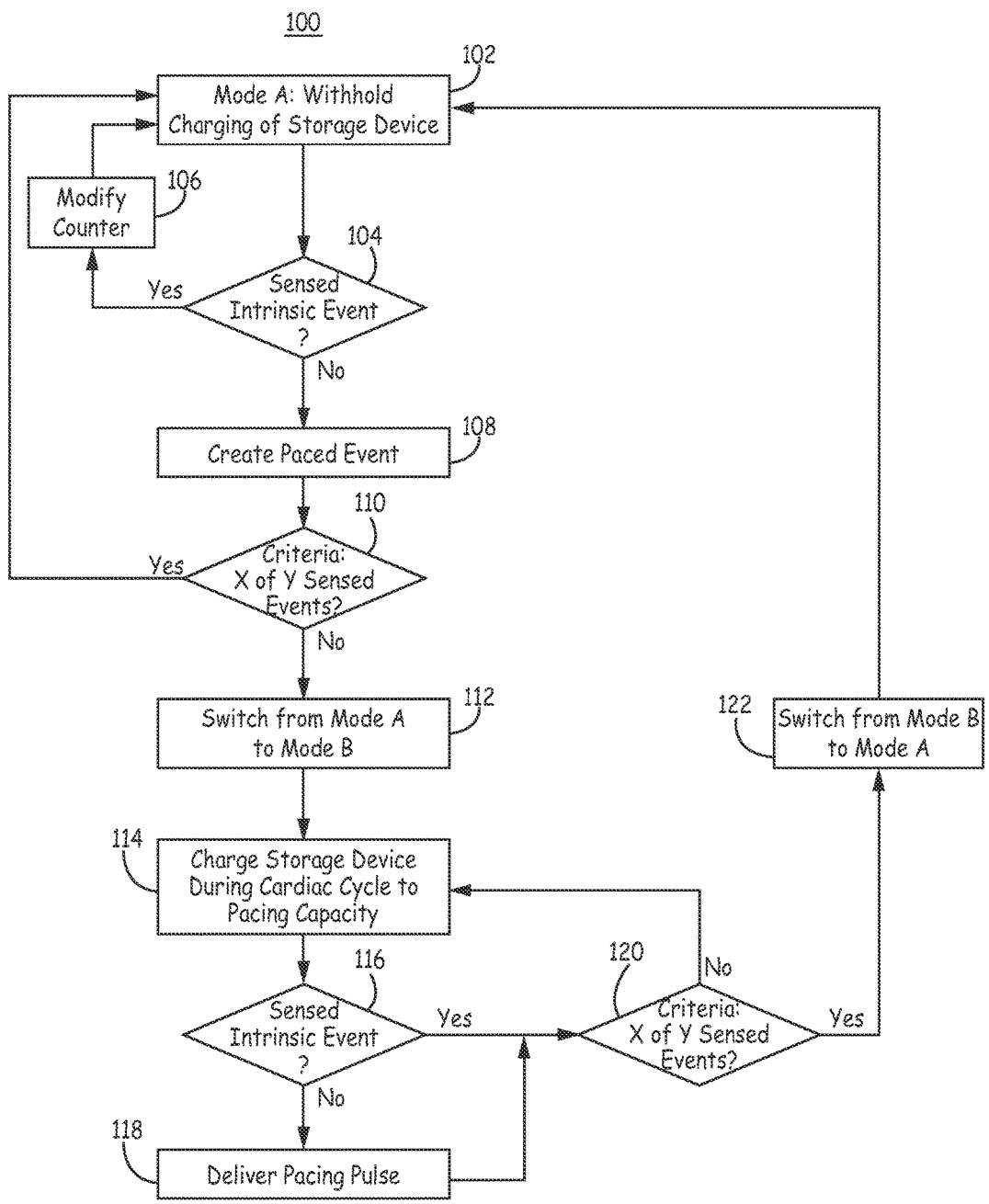
FIG. 5 is an exemplary flowchart outlining some tasks associated with a method for energy conservation performed in an implantable medical device in accordance with an embodiment.

FIG. 5 is an exemplary flowchart outlining some tasks that may be performed in accordance with aspects of the present disclosure whereby energy conservation is utilized to provide adequate pacing support to a patient while minimizing current drain in the IMD. In particular, the tasks pertain to the charging of an energy storage component, such as a capacitor, that holds energy for a stimulation therapy. In some embodiments, the tasks may be implemented as instructions to be executed by a processor such as processing module 60 (FIG. 4) or any other desirable control device. It should be understood that the reference to the components of circuitry 16 in FIG. 4 in the description of flowchart 100 is made simply for ease of discussion.

In conventional devices, one or more capacitor(s) are charged up in anticipation of delivering a pacing pulse and the energy in the capacitor is delivered if a pace is warranted. Often, an intrinsic event occurs prior to the programmed time for delivery of the pacing pulse and thereby inhibits delivery of the pacing pulse. When the pacing pulse is inhibited, the energy stored in the capacitor(s) must be stored for a longer duration as compared to if the pacing pulse were to be delivered in every cardiac cycle. As a result of extending the storage time, the energy in the capacitor bleeds off thereby requiring an additional recharge of the capacitor. This means that even if a device never delivers a pace, it can still lose a significant amount of its energy due to charging the pacing capacitors. The exemplary method 100 may be employed to minimize the capacitor energy losses that are associated with storage of energy within the capacitor for durations that are longer than necessary. For ease of description, the techniques of the method 100 will be described in conjunction with an IMD that provides a pacing pulse to ventricle 32 of a patient 36 (FIGS. 1, 2) it being understood that the same can be employed for left ventricular pacing or atrial pacing.

In task 102 of the outlined method 100, a selection is made between two or more charging modes that are provided in the IMD. The initial selection of the charging mode may be performed to optimize the current drain in the IMD. In the exemplary method 100, charging mode A is defined as a mode in which the output capacitor 80 will not be charged until a cardiac cycle has elapsed. Generally, charging mode A may be utilized in conjunction with pacing modes whereby the IMD permits an entire cardiac cycle to elapse without a sensed intrinsic ventricular (or atrial) event. Alternatively, the charging mode A may be utilized in conjunction with pacing modes that extend the patient's escape interval, e.g., through a hysteresis feature that gives the heart an opportunity to beat on its own before the pacemaker intervenes by increasing the base pacing interval by the hysteresis interval.

In one embodiment, charging mode A is implemented by maintaining the capacitor in a discharged state during the AV interval following a sensed or paced atrial event. At task 104, a sensing channel of the IMD is monitored to detect the occurrence of an intrinsic event during the cardiac cycle. For simplicity, this disclosure will describe the intrinsic event in relation to a depolarization of the right ventricle of the patient 36. However, those skilled in the art are familiar with the detection of other intrinsic events in a patient's heart such as left ventricular or atrial events.

Returning to task 104, the IMD will establish a ventricular pacing escape interval that is initiated for each cardiac cycle subsequent to a sensed or paced atrial event. Sensing of an R-wave within the duration of the escape interval for any given cardiac cycle (YES) will reset the escape interval and the IMD continues to operate in the mode A. In other words, the capacitor remains in the discharged state. However, if an R-wave is not detected within the duration of the escape interval and thus the cardiac cycle elapses without a sensed intrinsic event, i.e., ventricular in this example, a pacing pulse may be generated.

Following the detection of the sensed event, a sensed event counter is incremented to track the number of cycles that have an intrinsic sensed event (X) relative to a predetermined number of consecutive cycles (Y). For example, the number of cycles with a sensed intrinsic event (X) will be reset when the IMD is implanted and a sensed intrinsic event will increment the event counter by 1. The count of the consecutive cycles (Y) will of course be incremented at the end of each consecutive cycle. As will be described below in more detail, the predetermined number of consecutive cycles (Y) may be selected based on the patient's treatment regimen.

At task 108, a paced event is created. To create the paced event, the charging circuit initiates the charging of the capacitor from the discharged state to a pacing capacity. In other words, the charging circuit draws energy from the power source that is sufficient to store a stimulation pulse voltage in the capacitor that has enough energy to induce an evoked response. Although it is not illustrated in the figure, it should be understood that a paced event counter may be utilized in addition to, or instead of, the sensed event counter. Such a paced event counter could be implemented to track the number of cycles that are paced relative to a predetermined number of consecutive cycles.

According to decision point 110, an evaluation is made to determine whether the charging circuit should continue to operate in the charging mode A. The evaluation is based on a criterion relating to the count of the number of sensed intrinsic events (X) relative to the predetermined number of consecutive cycles (Y), where X and Y are integer numbers that are greater than one, and X is equal to or greater than one and Y is greater than or equal to X. The evaluation will involve a comparison to determine whether the number of sensed events is at least equal to the integer number X over the consecutive number of cycles Y, as defined in the criterion X of Y. When this criterion is met, the method continues operation in mode A (task 102). In an exemplary embodiment, X is two (2) and Y is three (3). In another embodiment, X is two (2) and Y is four (4). In another embodiment, X is three (3) and Y is four (4). In another embodiment, X is four (4) and Y is five (5). In another embodiment, X is seven (7) and Y is nine (9). In another embodiment, X is seventeen (17) and Y is twenty nine (29). In another embodiment, X is seventy one (71) and Y is eighty two (82). It should be understood that the above values are provided merely for illustration; the specific criteria for any given patient will be predicated on providing adequate pacing support while minimizing energy losses due to leakage currents that are associated with prolonged storage of energy in a capacitor.

The criteria for the evaluation at task 110 may be defined during the device configuration and/or during the operation of the implanted IMD. For example, programmer 40 may be utilized to transmit the criterion to the implanted IMD or to modify the criterion subsequent to the implantation. The selected criterion may be based on a given patient's treatment regimen or as a function of the desired longevity of the IMD. For example, commonly assigned U.S. Pat. No. 8,755,884, issued on Jun. 17, 2014 to Demmer, which is incorporated herein by reference in its entirety, describes methods whereby baseline and offset rates are established via dynamic input from rate response sensors and electrodes to provide pacing support to a patient.

If the result of the evaluation at 110 is that the criterion has not been met, a change in the charging mode is performed at task 112. In the exemplary embodiment, the IMD charging mode is changed from mode A to mode B. Charging operation under mode B will differ from the charging operation under mode A.

Turning to task 114, the capacitor charging is initiated during a given cardiac cycle and the capacitor is charged up to store the stimulation pulse voltage that will be delivered within the same, given, cardiac cycle upon the elapsing of the given cardiac cycle. Thus unlike the charging operation in mode A where the capacitor remains in the discharged state until the cardiac cycle has elapse, the charging operation in mode B will initiate the charging of the capacitor during the cardiac cycle such that the capacitor is charged up to the pacing state at the conclusion of the cardiac cycle. Of course, this stimulation pulse energy will be delivered unless an intrinsic event is sensed as will be outlined in more detail below.

Although not shown in the FIG. 5, it should be understood that the event counter may be reset in conjunction with the mode switch in accordance with some embodiments. However, in other embodiments, the reset may only be performed in conjunction with a mode switch that reverts back to mode A (e.g., no reset from mode A to mode B, with a reset when the mode switches next from mode B to mode A) as will be described below.

The sensing channel of the IMD will be monitored to detect the occurrence of an intrinsic event during the cardiac cycle (task 116). If an intrinsic event is not sensed within the duration of the given cardiac cycle (NO), the energy stored in the capacitor will be delivered in the form of a stimulation pulse therapy to induce an evoked response (task 118). However, a sensed intrinsic event (YES) will result in the withholding of the stimulation pulse therapy. Here, again, the number in the sensed event counter will be incremented by one (1).

Decision point 120 is similar to decision point 110 in that an evaluation is made to determine whether the number of sensed intrinsic events is at least equal to the number X for the predetermined number of consecutive cycles (Y), as defined in the criterion (X) of (Y). If the result of the evaluation is that the criterion has not been met, the method continues operation in mode B (task 114).

If the result of the evaluation at decision point 120 is that the criterion has been met, a change in the charging mode is performed at task 122. Additionally, the event counter may be reset in conjunction with the mode switch.

In the exemplary embodiments described herein, the IMD charging mode is changed from mode B to mode A. However, additional embodiments may employ more than two charging modes, e.g., mode A, mode B, mode C, etc. Similar to the two modes described in conjunction with FIG. 5, the charging operation under each mode may be different and different criteria may be employed to maintain the operation under each of those modes.

Figure 6:
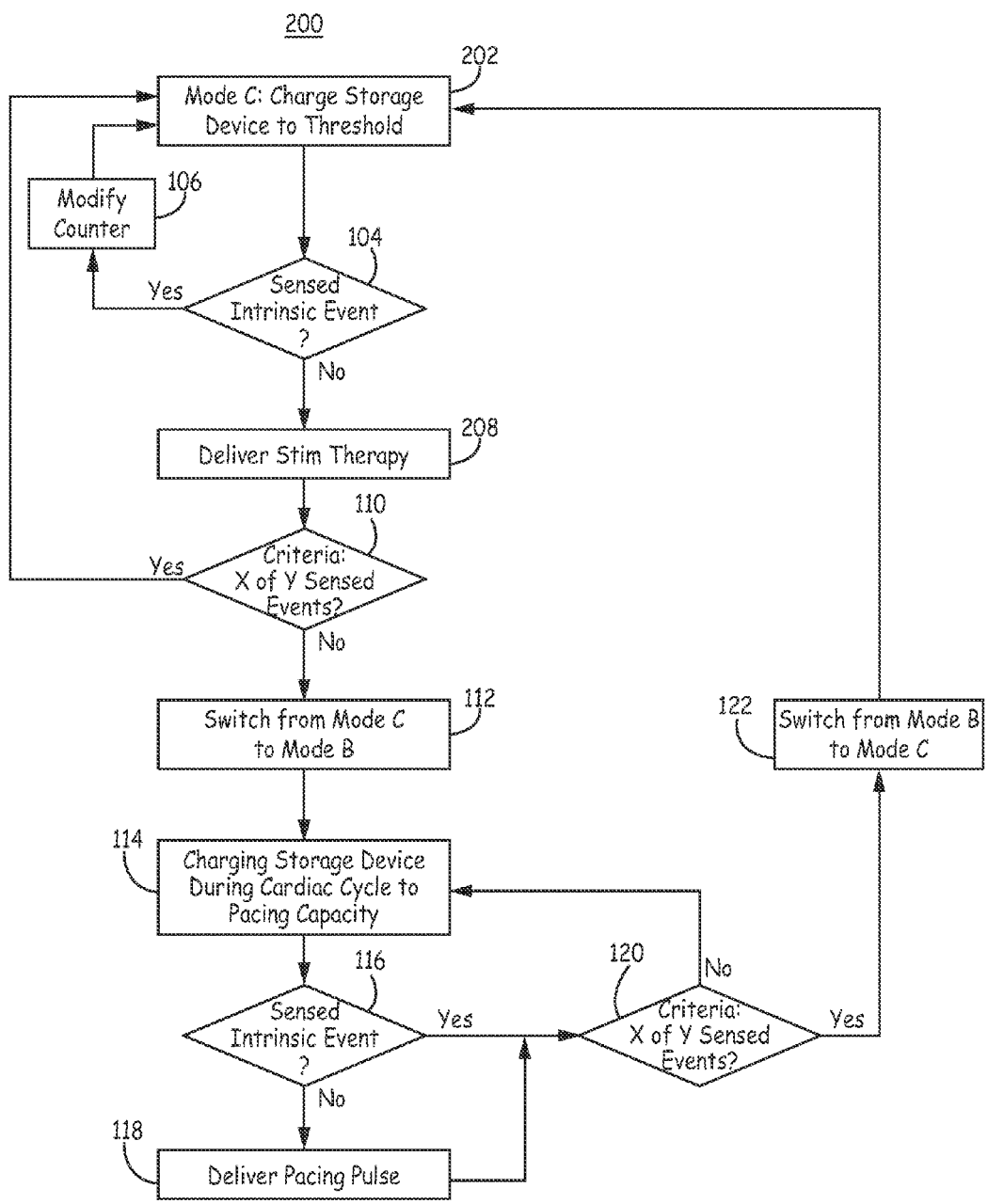
FIG. 6 is an exemplary flowchart outlining some tasks associated with a method for energy conservation performed in an implantable medical device in accordance with an alternative embodiment.

Accordingly, FIG. 6 depicts an exemplary flowchart outlining an alternative method in accordance with aspects of the present disclosure whereby energy conservation is utilized to provide adequate pacing support to a patient while minimizing current drain in the IMD. The tasks may be implemented as instructions to be executed by a processor such as processing module 60 (FIG. 4) or any other desirable control device. For ease of discussion, the flowchart 200 will be described in conjunction with the circuitry 16 of FIG. 4.

For ease of discussion, the tasks in FIG. 6 that are similar to those in FIG. 5 have been numbered with like numerals and the reader is referred to the description of FIG. 5 for a detailed description of those tasks. It should also be understood that although the figures are described as separate embodiments, the tasks in the embodiment of FIG. 5 may be substituted or added to the tasks in the embodiment of FIG. 6, or vice versa.

At task 202 of the outlined method 200, a selection is made between two or more charging modes that are provided in the IMD. In the exemplary method 200, charging mode C is defined as a mode in which the output capacitor 80 will not be charged until a cardiac cycle has elapsed. As illustrated in FIG. 6, the charging operation under mode C will differ from the charging operation under mode B (described in FIG. 5 in more detail).

In one embodiment, the capacitor charging under charging mode C is implemented by charging the capacitor to a first threshold capacity during an AV interval following a sensed or paced atrial event. The charge energy may be drawn from the power source (72). The first threshold capacity is less than a pacing capacity that defines the stimulation pulse voltage required to induce an evoked response. In an example, the first threshold capacity may be in the range of five percent (5%) to ninety-five percent (95%) of the pacing capacity of the capacitor. In another example, the first threshold capacity may be any voltage that does not have sufficient energy to induce an evoked depolarization response.

Based on the current capacity of the power source, an evaluation of the charging duration; that is, the time that it will take to charge up the capacitor from the discharged state to the first threshold capacity or the pacing capacity, and similarly from the first threshold capacity or the pacing capacity. This charging duration may be employed to determine the point in time when the charging may be initiated along the cardiac cycle so as to adequately charge up the capacitor to the desired level by or at the completion of that same cardiac cycle. In other words, the charging will begin at a time corresponding to the cardiac cycle duration less the charging duration, such that the charging of the capacitor is charged up to the pacing capacity at the expiration of the cardiac cycle duration. Doing so will eliminate or minimize the bleed off of energy from the capacitor.

In an alternative embodiment, the capacitor charging under task 202 may be implemented by trickle-charging the capacitor. In the example embodiment, the energy drawn during the trickle-charging of the capacitor may be generated by an energy harvesting device (power source 72).

As described with reference to FIG. 5, a sensing channel of the IMD is monitored to detect the occurrence of an intrinsic event during the cardiac cycle (104). At task 208, the capacitor is charged to a pacing capacity. It should be appreciated that the duration of charging the capacitor to the pacing capacity at task 208 will be shorter than the duration of time it takes to charge the capacitor to the same pacing capacity at task 108. This is because the capacitor will have been charged up to a predetermined threshold prior to beginning the charging at task 208. Upon charging the capacitor to the pacing capacity, a stimulation pulse voltage is delivered if a sensed intrinsic event has not been detected at the conclusion of the cardiac cycle. Therefore, the capacitor charging may be initiated just prior to, or even at the completion of the cardiac cycle. In other words, the charging of the capacitor can be delayed until delivery of the pacing pulse has been deemed to be necessary based on non-occurrence of the intrinsic event.

Providing software, firmware and hardware to accomplish the present invention, given the disclosure herein, is within the abilities of one of skill in the art. For the sake of brevity, conventional techniques related to ventricular/atrial pressure sensing, signal processing, telemetry, and other functional aspects of the systems (and the individual operating components of the systems) may not be described in detail herein. The connecting lines shown in the various figures contained herein are intended to represent example functional relationships and/or physical couplings between the various elements. It should be noted that many alternative or additional functional relationships or physical connections may be present in an embodiment of the subject matter.

The description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although the schematics shown in the figures depict exemplary arrangements of elements, additional intervening elements, devices, features, or components may be present in an embodiment of the depicted subject matter.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

What is claimed is:

1. An implantable medical device, comprising:
 a sense amplifier configured to sense intrinsic cardiac events;
 an output capacitor;
 a charging circuit coupled to the output capacitor;
 a processor coupled to the sense amplifier and to the charging circuit, wherein the processor is configured to selectively operate the charging circuit in a first mode or a second mode, wherein the charging circuit is controlled to withhold charging of the output capacitor until a given cardiac cycle elapses without a sensed intrinsic cardiac event during operation in the first mode, and wherein the charging circuit is controlled to initiate charging of the output capacitor within the given cardiac cycle prior to elapsing of the given cardiac cycle during operation in the second mode.

2. The implantable medical device of claim 1, wherein in the first mode, the charging circuit initiates charging of the output capacitor responsive to the given cardiac cycle elapsing to generate a pacing pulse.

3. The implantable medical device of claim 1, wherein the first mode is selected responsive to satisfying a predetermined criteria for the sensed intrinsic cardiac events, the criteria including sensing x of y successive intrinsic cardiac events, x being equal to or greater than one and y being greater than or equal to x.

4. The implantable medical device of claim 3, wherein x is two and y is four.

5. The implantable medical device of claim 3, wherein x is four and y is five.

6. The implantable medical device of claim 3, wherein x is seven and y is nine.

7. The implantable medical device of claim 3, wherein the second mode is selected responsive to the predetermined criteria for the sensed intrinsic cardiac events not being satisfied.

8. The implantable medical device of claim 1, wherein the processor operates the charging circuit in the first mode and switches to the second mode in response to failing to satisfy a predetermined criteria, the criteria including sensing x of y successive intrinsic cardiac events, x being equal to or greater than one and y being greater than or equal to x.

9. The implantable medical device of claim 1, wherein the cardiac cycle is defined between two successive atrial events.

10. The implantable medical device of claim 1, wherein the cardiac cycle is defined between two successive ventricular events.

11. The implantable medical device of claim 1, wherein the processor is further configured to establish a charging duration for charging of the output capacitor from a discharged state to the pacing capacity, wherein the processor controls the charging circuit to initiate the charging at a time such that the charging duration will end at the same time as the termination of the duration of the cardiac cycle.

12. An implantable medical device, comprising:
means for sensing intrinsic cardiac events;
an output capacitor configured to store a stimulation pulse voltage configured to induce an evoked response; and
means for charging the output capacitor configured to operate in a charging mode selected between a first mode and a second mode, wherein the charging means is controlled to withhold charging of the output capacitor until a given cardiac cycle elapses without a sensed intrinsic cardiac event during operation in the first mode, and wherein the charging means is controlled to initiate charging of the output capacitor within the given cardiac cycle prior to elapsing of the given cardiac cycle during operation in the second mode.

13. The implantable medical device of claim 12, further comprising means for evaluating the sensed intrinsic cardiac events with respect to a predetermined criteria, wherein the charging mode is selected based on a result of an evaluation performed by the means for evaluating.

14. The implantable medical device of claim 13, wherein the charging means is selectively operable in the first mode responsive to the predetermined criteria being satisfied, and the charging means is selectively operable in the second mode responsive to the predetermined criteria not being satisfied.

15. The implantable medical device of claim 13, wherein the predetermined criteria comprises sensing x of y successive intrinsic cardiac events, x being equal to or greater than one and y being greater than or equal to x.

16. The implantable medical device of claim 13, wherein x is two and y is four.

17. The implantable medical device of claim 13, wherein x is seven and y is nine.

18. The implantable medical device of claim 12, wherein the cardiac cycle is defined between two successive atrial events.

19. The implantable medical device of claim 12, wherein the cardiac cycle is defined between two successive ventricular events.

20. The implantable medical device of claim 12, wherein in the first mode, the charging circuit initiates charging of the output capacitor responsive to the given cardiac cycle elapsing to generate the stimulation pulse voltage.

* * * * *